(12) United States Patent
Komachi et al.

(10) Patent No.: US 6,582,359 B2
(45) Date of Patent: Jun. 24, 2003

(54) ENDOSCOPE APPARATUS FOR INSIDE WALL OF BLOOD VESSEL

(75) Inventors: Yuichi Komachi, Akishima (JP); Katsuo Aizawa, Yokohama (JP); Shin Ishimaru, Tokyo (JP); Tsuneyuki Nagae, Tokyo (JP); Atsushi Utsumi, Kawanishi (JP)

(73) Assignee: Machida Endoscope Co., Ltd. (JP)

( * ) Notice: Subject to any disclaimer, the term of this patent is extended or adjusted under 35 U.S.C. 154(b) by 0 days.

(21) Appl. No.: 09/960,690

(22) Filed: Sep. 21, 2001

(65) Prior Publication Data

US 2002/0042555 A1 Apr. 11, 2002

(30) Foreign Application Priority Data

Oct. 6, 2000 (JP) .................................... 2000-307030

(51) Int. Cl.⁷ ................................................ A61B 1/04
(52) U.S. Cl. ...................... 600/115; 600/116; 600/170; 600/171; 604/96.01
(58) Field of Search ................................ 600/115, 116, 600/170, 171, 121; 604/96.01

(56) References Cited

U.S. PATENT DOCUMENTS 3,818,902 A * 6/1974 Kinoshita et al. ............ 385/118
4,224,929 A * 9/1980 Furihata ....................... 600/107
5,409,483 A * 4/1995 Campbell et al. ............. 606/13

FOREIGN PATENT DOCUMENTS

| JP | 3-264037 | 11/1991 |
| JP | 3-264038 | 11/1991 |
| JP | 8-322785 | 12/1996 |

OTHER PUBLICATIONS

PTCA Balloon Catheter, Omni Pass, a catalogue issued by Johnson and Johnson Company, Sep. 2000.

* cited by examiner

Primary Examiner—John Mulcahy
(74) Attorney, Agent, or Firm—Eugene Stephens & Associates

(57) ABSTRACT

An endoscope apparatus has a side view endoscope 10 for side viewing an object in a radial direction of a distal end constitutional portion 14 and a balloon catheter 40. With an insert portion 13 of a side view endoscope 10 inserted in an insert tube 41 of the balloon catheter 40, the balloon catheter 40 is inserted into a blood vessel B. The insert tube 41 is provided at its distal end with a transparent balloon 42. This balloon 42 encloses the distal end constitutional portion 14. By feeding air (fluid) to this balloon 42, the balloon 42 is expanded so as to be urged against an inside wall of the blood vessel B. This causes the blood to be discharged between the inside wall of the blood vessel B and the balloon 42, thus enabling to observe the inside wall of the blood vessel B through the side view endoscope 10.

3 Claims, 3 Drawing Sheets

ENDOSCOPE APPARATUS FOR INSIDE WALL OF BLOOD VESSEL

BACKGROUND OF THE INVENTION

This invention relates to an endoscope apparatus for observing an inside wall of a blood vessel.

If an inside wall of a blood vessel could be observed through an endoscope, it would be of great help to diagnosis and treatment of diseases such as myocardial infarction, cerebral thrombosis. However, this is not an easy job to carry out because the view field of the endoscope is covered with blood in the blood vessel.

SUMMARY OF THE INVENTION

The present invention has been accomplished in view of the above situation. According to a first feature of the present invention, there is provided an endoscope apparatus for an inside wall of a blood vessel comprising (a) a side view endoscope including a main body portion, a flexible insert portion extending from the main body and a distal end constitutional portion disposed at a distal end of the insert portion, the insert portion being capable of being inserted into the blood vessel, the distal end constitutional portion being provided at a peripheral surface thereof with an illuminating window and an observing window, a light guide for transmitting an illuminating light to the illuminating window and an image guide for transmitting an imaging light which is made incident to the observing window being inserted into the insert portion, thereby enabling to observe the inside wall of the blood vessel located in a radial direction of the distal end constitutional portion, (b) a balloon for enclosing the distal end constitutional portion, at least a part of the balloon which covers the illuminating window and the observing window being transparent, (c) a flexible insert tube extending along the insert portion, an internal space of the distal end of the insert tube being in communication with a space between the balloon and the distal end constitutional portion, and (d) fluid feeding means connected to a basal end portion of the insert tube and adapted to feed a fluid to the balloon through the insert tube.

Owing to this feature, by expanding the balloon so as to be urged against the inside wall of the vessel, the inside wall of the blood can be observed.

According to a second feature of the present invention, there is provided an endoscope apparatus for an inside wall of a blood vessel, wherein, in addition to the first feature, the insert tube and the balloon are integrally continuous with each other thereby constituting a balloon catheter, the insert portion of the side view endoscope is inserted into the insert tube, a sealing is provided between the balloon catheter on the basal side and the side view endoscope, and a space formed between the insert tube and the insert portion serves as a flow passage for guiding the fluid to the balloon.

Owing to this feature, by inserting the insert portion into the balloon catheter and further into the blood vessel, the balloon can be expanded serving the space formed between the inner periphery of the insert tube and the outer periphery of the insert portion as a flow passage.

According to a third feature of the present invention, there is provided an endoscope apparatus for an inside wall of a blood vessel, wherein, in addition to the second feature, the balloon is transparent over its entire periphery, and the insert portion and distal end constitutional portion of the side view endoscope are rotatable with respect to the balloon catheter about an axis of the insert portion and the distal end constitutional portion.

Owing to this feature, the inside wall of the blood vessel can be observed over 360 degrees.

According to a fourth feature of the present invention, there is provided an endoscope apparatus for an inside wall of a blood vessel, wherein, in addition to the third feature, the distal end constitutional portion includes an extending shaft portion disposed on a more forward side rather than the illuminating window and the observing window and projecting in an axial direction, and the balloon is provided at its distal end with a shaft receiving portion for rotatably receiving the extending shaft portion.

Owing to this feature, the distance between the distal end constitutional portion and an observing part of the inside wall of the blood vessel, and thus the focal distance can be maintained constant irrespective of angle.

According to a fifth feature of the present invention, there is provided an endoscope apparatus for an inside wall of a blood vessel, wherein, in addition to the first feature, the distal end constitutional portion receives therein a pair of illuminating prisms for refracting the illuminating light delivered by the light guide towards the illuminating window and an imaging light prism for refracting the imaging light made incident to the observing window towards the distal end of the image guide, the pair of illuminating prisms being arranged in such a manner as to sandwich the imaging light prism therebetween.

Owing to this feature, illuminating light can be obtained from two sides of the observing part and there can be obviated such an inconvenience that one side of the observing part becomes dark and therefore, difficult to be observed.

According to a sixth feature of the present invention, there is provided an endoscope apparatus for an inside wall of a blood vessel, wherein, in addition to the fifth feature, the pair of illuminating prisms are arranged such that optical axes of the illuminating lights after refracted are intersected with each other on an optical axis of the imaging light before refracted.

Owing to this feature, the observing part can be illuminated more brightly.

DETAILED DESCRIPTION OF THE INVENTION

Figure 1:
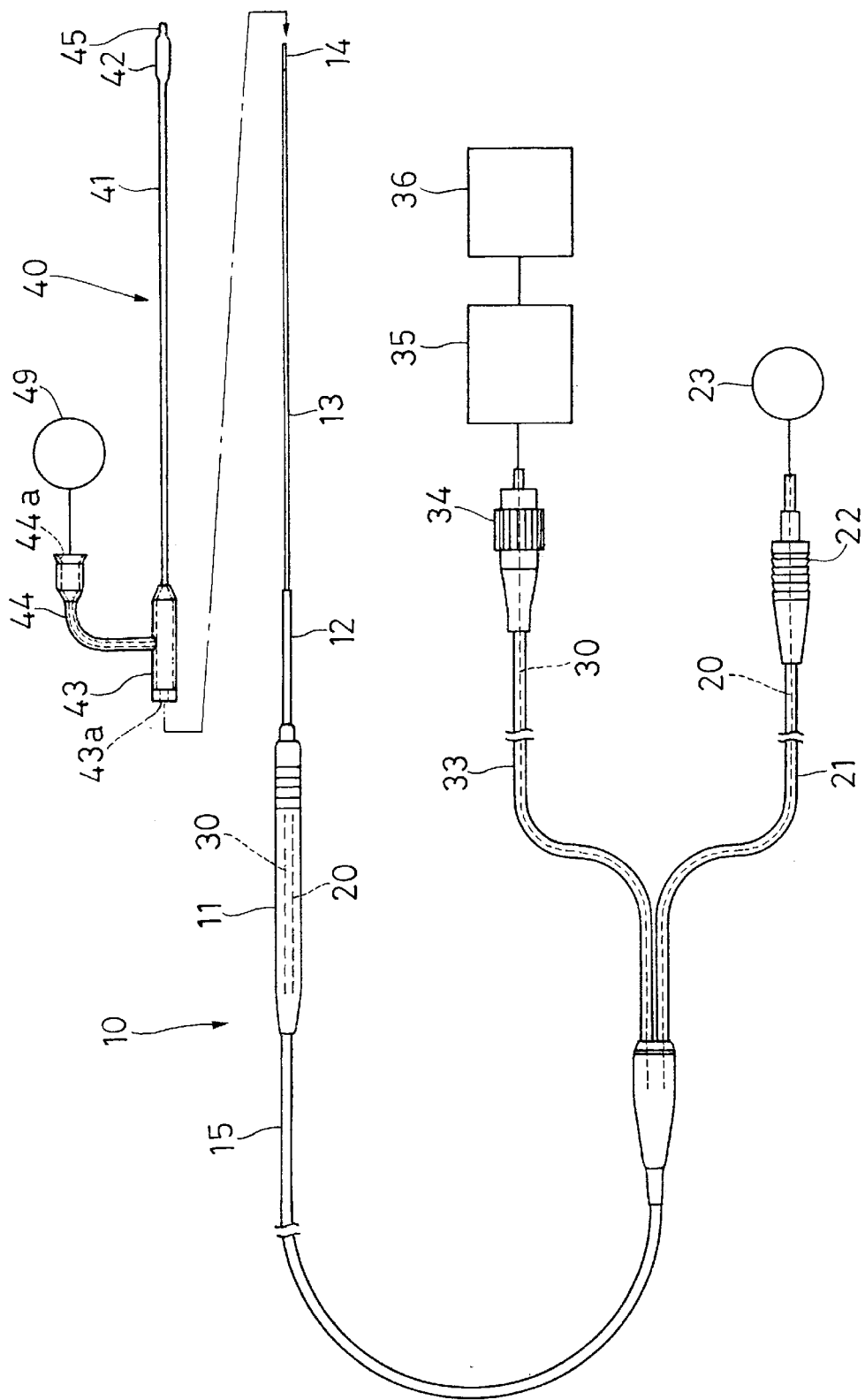
FIG. 1 is a side view showing an endoscope apparatus according to one embodiment of the present invention, in which a side view endoscope and a balloon catheter are separately from each other.

One embodiment of the present invention will be described hereinafter with reference to the accompanying drawings. As shown in FIG. 1, an endoscope apparatus for an inside wall of a blood vessel includes a side view endoscope 10 and a balloon catheter 40.

The side view endoscope 10 will now be described. The side view endoscope 10 includes a pen grip 11, an insert portion 13 connected to a distal end of the pen grip 11 through a stainless steel-made reinforcing tube 12 and a distal end constitutional portion 14 disposed at the distal end of the insert portion 13. The pen grip 11 and the reinforcing tube 12 constitutes a "main body portion".

Figure 2:
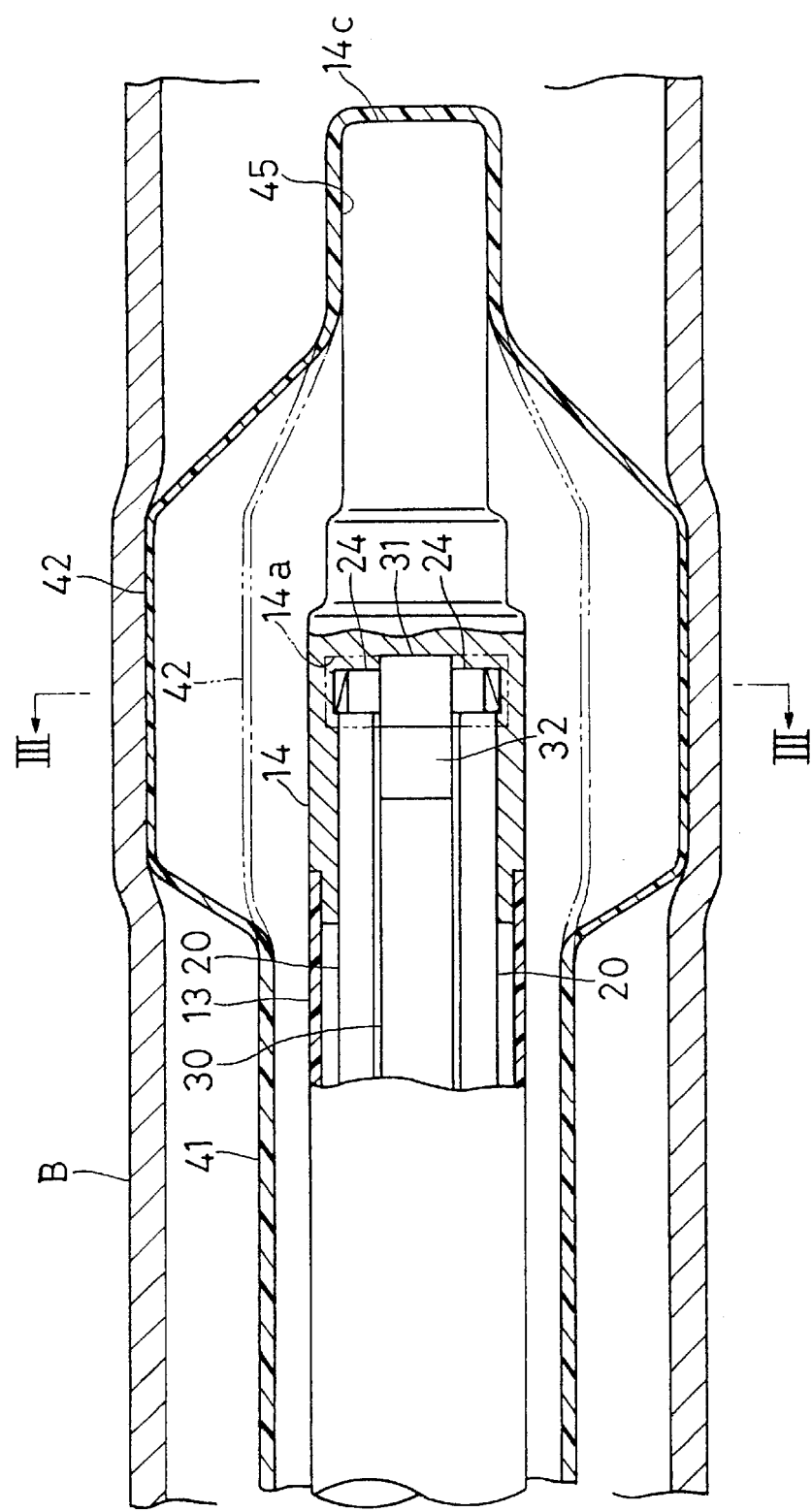
FIG. 2 is a sectional view showing a distal end portion of the above apparatus, which is in a state of use for observing a blood vessel.
Figure 3:
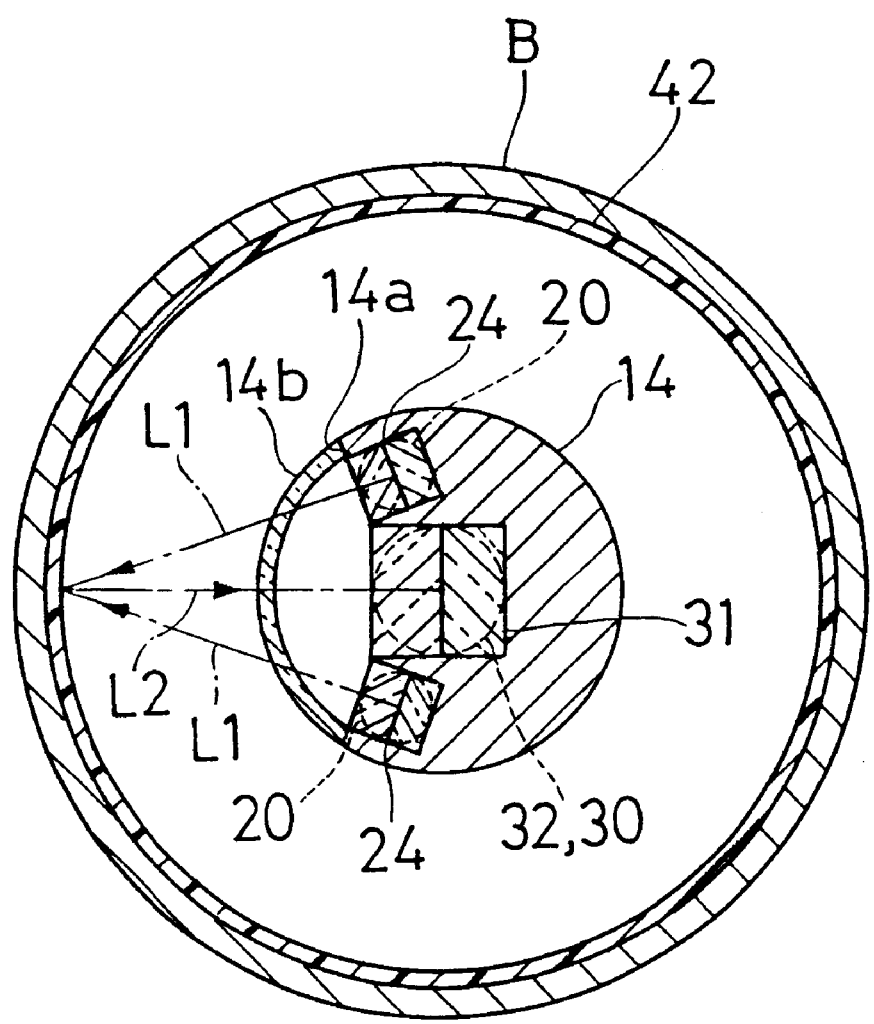
FIG. 3 is a sectional view of the apparatus taken on line of III—III of FIG. 2.

As shown in FIGS. 2 and 3, the outside diameter of the insert portion 13 is smaller than the inside diameter of a blood vessel B of an object to be observed and is, for example, 1.6 mm. The distal end constitutional portion 14 is cylindrical and has a window 14a (illuminating window and observing window which are integrally connected to each other) formed in a peripheral surface thereof. The window 14a is provided with a transparent window glass 14b.

A light transmitting system of the side view endoscope 10 will now be described. As shown in FIG. 1, the pen grip 11 is continuous at a basal end thereof with a common code 15 from which a light cord 21 and an image cord 33 are branched. The light code 21 is connected to a light source 23 through a light plug 22.

The light plug 22, the light cord 21, the common cord 15, the pen grip 11, the reinforcing tube 12 and the insert portion 13 receive therein a light guide 20 composed of a flux of optical fibers. As shown in FIGS. 2 and 3, the distal end portion of the light guide 20 is divided into two fluxes and reaches the distal end constitutional portion 14.

One pair of illuminating prisms 24 are received in the distal end constitutional portion 14. Those pair of illuminating prisms 24 are connected, respectively, to distal ends of the two fluxes of the light guide 20. Each prism 24 is adapted to refract the illuminating light coming from the light source 23 along the light guide 20 towards the window 14a. The refractive index Nd of the prism 24 is preferably 1.7 or larger, and more preferably 1.9 or larger.

The pair of prisms 24 are arranged such that the optical axes L1 (outgoing optical axes of the illuminating prism 24) of the illuminating light after refracted are intersected with each other on the optical axis L2 (incoming optical axis of an imaging light prism 31 as later described) of the imaging light which is made incident to the window 14a. An angle formed between each illuminating axis L1 and the imaging light axis L2 is set to a number ranging from, for example, 10 degrees to 40 degrees.

An imaging light prism 31 is disposed between the pair of illuminating light prisms 24. This prism 31 is adapted to refract the imaging light towards the basal portion of the distal end constitutional portion 14. The refractive index Nd of the prism 31 is, like the illuminating light prism 24, preferably 1.7 or larger and more preferably 1.9 or larger.

An image guide 30 is disposed more on the basal side rather than the prism 31 through a selfox lens 32 (objective lens). The image guide 30 is received in the distal end constitutional portion 14, the insert portion 13, the reinforcing tube 12, the pen grip 11, the common cord 15 and the image cord 33 which are all located more on the basal side rather than the selfox lens 32 and reaches the image connector 34. This image connector 34 is connected to an image processor 35 to which a TV monitor 36 is connected.

The balloon catheter 40 will now be described. The balloon catheter 40 includes a flexible insert tube 41, a balloon 42 integrally continuous with the distal end portion of the insert tube 41 and a hand side tube 43 which has a thick wall and an enlarged diameter and which is integrally continuous with the basal side of the insert tube 41. This balloon catheter 40 is made of a transparent resin. That is to say, the balloon 42 is transparent over its entire periphery.

The outside diameter of the insert tube 41 is 3.5 mm maximum so as to be entered into the blood vessel B. The insert portion 13 of the side view endoscope 10 is inserted into the insert tube 41, and the reinforcing tube 12 is inserted into the hand side tube 43. The hand side tube 43 is provided at the inner periphery of its basal end with a sealing portion 43a which is closely contacted with the reinforcing tube 12 so as to seal a space between the hand side tube 43 and the reinforcing tube 12 in the above-mentioned inserted state. This sealing portion 43a allows the rotation of the insert portion 13 about its axis while maintaining the sealing state.

The hand side tube 43 is provided at its outer periphery with a feeding connector 44. A port 44a is formed in the feeding connector 44. This port 44a is in communication with an internal space of the hand side tube 43 and thus an internal space of the insert tube 41. The port 44a is connected with an air feeding source 49 (fluid feeding source). Air (fluid) is fed into the balloon 42 from the air feeding source 49 through the port 44a and via the interior of the insert tube 41. The feeding connector 44 and the air feeding source 49 constitute a "fluid feeding means".

As shown in FIGS. 2 and 3, the balloon 42 has a thinner wall than the insert tube 41 and is expanded in a radial direction by pressure of the air (a state before the balloon is expanded is indicated by an imaginary line and a state after expansion is indicated by a solid line in FIG. 2). With the insert portion 13 inserted in the insert tube 41, the distal end constitutional portion 14 is located at the interior of the balloon 42. In other words, the balloon 42 encloses the distal end constitutional portion 14. The balloon 42 is provided at its distal end with a shaft receiving portion 45 having a thick wall. This shaft receiving portion 45 rotatably receives therein an extending shaft portion 14c projecting beyond the window 14a of the distal end constitutional portion 14.

A way of use of the endoscope apparatus thus constructed will now be described. The insert portion 13 is inserted into the balloon catheter 40 and this balloon catheter 40 is inserted into the blood vessel B. When the balloon 42 reaches a position to be observed of the blood vessel B, air is introduced between the balloon 42 and the distal end constitutional portion 14 from the air feeding source 49. This air pressure causes the balloon 42 to be expanded and urged against the inside wall of the blood vessel B over its entire periphery. By this, the blood between the blood vessel B and the balloon 42 can be discharged. As a result, after the illuminating light coming from the light source 21 is outputted from window 14a via the light guide 20 and the prism 24, it can pass through the transparent balloon 42 and illuminate the inside wall of the blood vessel B. And the imaging light of the illuminated inside wall can pass through the balloon 42 and be made incident to the window 14a. The incident imaging light sequentially passes through the prism 31, the selfox lens 32 and the image guide 30. It is then converted into a TV signal via an ocular lens and a signal converting portion, not shown, contained in an image processor 35 and displayed on the TV monitor 36. This makes it possible to observe the inside wall of the blood vessel B and thus, it can be of great help to diagnosis and treatment of diseases such as myocardial infarction, cerebral thrombosis.

Since the illuminating optical axes L1 are arranged on both sides of the imaging optical axis L2 in such a manner as to sandwich the imaging optical axis L2 therebetween, the observing part of the inside wall of the blood vessel can be illuminated from the both sides. This can avoid an occurrence of such an inconvenient state that one side of the observing part becomes dark and thus difficult to be observed. Moreover, since the pair of illuminating optical axes L1 are slanted in such a manner as to be intersected with each other on the imaging optical axis L2, the observing part can be illuminated more brightly, thus enabling to observe the observing part easily.

By rotating the pen grip 11 about its axis, the insert portion 13 and thus, the distal end constitutional portion 14 can be rotated. This makes it possible to observe the inside wall of the blood vessel B over 360 degrees. At that time, the distal end constitutional portion 14 can be maintained in a posture laid along a center axis of the balloon 42 by the extending shaft portion 14c and the shaft receiving portion 45. By this, the distance from the distal end constitutional portion 14 to the observing part and thus, the focal distance can be maintained constant irrespective of the angle.

After finish of observation, the air feeding source 49 is stopped and the port 44a is opened to release air. By doing so, the balloon 42 is contracted and brought away from the inside wall of the blood vessel. Thereafter, the balloon catheter 40 and the insert portion 13 are withdrawn from the blood vessel B.

It should be noted that the present invention is not limited to the above embodiment, and that many changes and modifications can be made in accordance with necessity.

For example, the distal end constitutional portion 14 may be provided, instead of the only one window 14a, with both an illuminating window for allowing the passage of illuminating light therethrough and an observing window for allowing the passage of imaging light therethrough which are arranged proximate to each other.

In the case where the insert portion is not rotated with respect to the balloon, it suffices that at least a part of the distal end constitutional portion which covers the illuminating window and the observing window is transparent.

It is accepted that the insert tube is inserted into the insert portion of the side view endoscope or the insert tube is disposed outside of the insert portion in parallel relation.

The fluid for expanding the balloon is not limited to air inasmuch as the fluid is transparent. The fluid may, of course, be liquid or gas but air.

What is claimed is:

1. An endoscope apparatus for an inside wall of a blood vessel comprising:
   (a) a side view endoscope including a main body portion, a flexible insert portion extending from said main body and a distal end constitutional portion disposed at a distal end of said insert portion, said insert portion being capable of being inserted into said blood vessel, said distal end constitutional portion being provided at a peripheral surface thereof with an illuminating window and an observing window, a light guide for transmitting an illuminating light to said illuminating window and an image guide for transmitting an imaging light which is made incident to said observing window being inserted into said insert portion, thereby enabling to observe the inside wall of the blood vessel located in a radial direction of said distal end constitutional portion;
   (b) a balloon for enclosing said distal end constitutional portion, at least a part of said balloon which covers said illuminating window and said observing window being transparent;
   (c) a flexible insert tube extending along said insert portion, an internal space of the distal end of said insert tube being in communication with a space between said balloon and said distal end constitutional portion;
   (d) fluid feeding means connected to a basal end portion of said insert tube and adapted to feed a fluid to said balloon through said insert tube;
   (e) said insert tube and said balloon being integrally continuous with each other thereby constituting a balloon catheter, said insert portion of said side view endoscope being inserted into said insert tube, a sealing being provided between said balloon catheter on the basal side and said side view endoscope, and a space formed between said insert tube and said insert portion serving as a flow passage for guiding the fluid to said balloon;
   (f) said balloon being transparent over its entire periphery, and said insert portion and distal end constitutional portion of said side view endoscope being rotatable with respect to said balloon catheter about an axis of said insert portion and said distal end constitutional portion; and
   (g) said distal end constitutional portion including an extending shaft portion disposed on a more forward side rather than said illuminating window and said observing window and projecting in an axial direction, and said balloon being provided at its distal end with a shaft receiving portion for rotatably receiving said extending shaft portion.

2. An endoscope apparatus for an inside wall of a blood vessel comprising:
   (a) a side view endoscope including a main body portion, a flexible insert portion extending from said main body and a distal end constitutional portion disposed at a distal end of said insert portion, said insert portion being capable of being inserted into said blood vessel, said distal end constitutional portion being provided at a peripheral surface thereof with an illuminating window and an observing window, a light guide for transmitting an illuminating light to said illuminating window and an image guide for transmitting an imaging light which is made incident to said observing window being inserted into said insert portion, thereby enabling to observe the inside wall of the blood vessel located in a radial direction of said distal end constitutional portion;
   (b) a balloon for enclosing said distal end constitutional portion, at least a part of said balloon which covers said illuminating window and said observing window being transparent;
   (c) a flexible insert tube extending along said insert portion, an internal space of the distal end of said insert tube being in communication with a space between said balloon and said distal end constitutional portion;
   (d) fluid feeding means connected to a basal end portion of said insert tube and adapted to feed a fluid to said balloon through said insert tube; and
   (e) said distal end constitutional portion receiving therein a pair of illuminating prisms for refracting the illuminating light delivered by said light guide towards said illuminating window and an imaging light prism for refracting the imaging light made incident to said observing window towards the distal end of said image guide, said pair of illuminating prisms being arranged in such a manner as to sandwich said imaging light prism therebetween.

3. An endoscope apparatus for an inside wall of a blood vessel according to claim 2, wherein said pair of illuminating prisms are arranged such that optical axes of the illuminating lights after refracted are intersected with each other on an optical axis of the imaging light before refracted.

* * * * *